US007011816B2

(12) United States Patent
Griffiths et al.

(10) Patent No.: US 7,011,816 B2
(45) Date of Patent: *Mar. 14, 2006

(54) LABELING TARGETING AGENTS WITH GALLIUM-68 AND GALLIUM-67

(75) Inventors: Gary L. Griffiths, Morristown, NJ (US); William J. McBride, Boonton, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 92 days.

This patent is subject to a terminal disclaimer.

(21) Appl. No.: 10/318,401

(22) Filed: Dec. 13, 2002

(65) Prior Publication Data

US 2003/0176784 A1    Sep. 18, 2003

Related U.S. Application Data

(60) Provisional application No. 60/342,104, filed on Dec. 26, 2001.

(51) Int. Cl.
*A61K 49/04* (2006.01)
(52) U.S. Cl. ............... 424/9.4; 424/1.11; 424/1.49; 424/1.65; 424/1.69; 424/9.1
(58) Field of Classification Search ............... 424/1.11, 424/1.49, 1.69, 1.65, 9.1, 9.3–9.8; 534/7, 534/10–16; 530/300, 331
See application file for complete search history.

(56) References Cited

U.S. PATENT DOCUMENTS

| 5,079,346 | A |   | 1/1992 | Kung |
| 5,256,395 | A |   | 10/1993 | Barbet et al. |
| 5,364,613 | A | * | 11/1994 | Sieving et al. ............... 424/9.3 |
| 5,639,439 | A |   | 6/1997 | Lee et al. |
| 6,071,490 | A | * | 6/2000 | Griffiths et al. ............ 424/1.49 |
| 2003/0124057 | A1 | * | 7/2003 | Griffiths et al. ............ 424/1.49 |
| 2003/0198595 | A1 | * | 10/2003 | Goldenberg et al. ....... 424/1.49 |
| 2004/0043030 | A1 | * | 3/2004 | Griffiths et al. .......... 424/178.1 |

FOREIGN PATENT DOCUMENTS

| WO | WO 94/04485 A1 | 3/1994 |
| WO | WO 98/04293 A1 | 2/1998 |
| WO | WO 99/56792 A1 | 11/1999 |

OTHER PUBLICATIONS

Henze et al., "PET Imaging of Somatostatin Receptors Using [$^{66}$GA]DOTA-$_D$-PHE$^1$Tyr$^3$Octreotide: First Results in Patients with Meningiomas," *Journal of Nuclear Medicine: Official Publication, Society of Nuclear Medicine* (Jul. 2001), vol. 42, No. 7, pp. 1053-1056, XP002245466, ISSN: 0161-5505.
Heppeler et al., "Receptor Targeting for Tumor Localisation and Therapy with Radiopeptides," *Current Medicinal Chem istry* (2000), vol. 7, pp. 971-994, Bentham Science Publishers, XP000982225, ISSN: 0929-8673.
Shizuko Ambe, "$^{68}$Ge-$^{68}$Ga Generator with Alpha-ferric Oxide Support," *Appl. Radiat. Isot.; Int. J. Radiat. Appl. Instrum. Part A.*, 1988, pp. 49-51, vol. 39, No. 1, ®Pergamon Press Great Britain.
David A. Goodwin et al., "Rapid Synthesis and Quality Control of $^{68}$Ga-labeled Chelates for Clinical Use," *Nucl. Med. Biol.*, 1994, pp. 897-899, vol. 21, No. 6, ®Pergamon Press Great Britain.
Mark A. Green et al., "Potential Gallium-68 Tracers for Imaging the Heart with PET: Evaluation of Four Gallium Complexes with Functionalized Tripodal Tris (Salicylaldimine) Ligands," *Journal of Nuclear Medicine*, 1993, pp., 228-233, vol. 34., No. 2.
Donald J. Hnatowich, A Method for the Preparation and Quality Control of $^{68}$Ga Radiopharmaceuticals, *Journal of Nuclear Medicine*, 1975, pp. 764-768, vol. 16, No. 8.
Gabor Klivenyi et al., "Gallium-68 Chelate Imaging of Human Colon Carcinoma Xenografts Pretargeted with Bispecific Anti-CD44$_{v6}$/Anti-Calluim Chelate Antibodies," *The Journal of Nuclear Medicine*, 1998, pp. 1769-1776, vol. 39, No. 10.
S. Kulprathipanja et al., "A Method for Determining the pH Stability Range of Gallium Radiopharmaceuticals," *The International Journal of Applied Radiation and Isotopes*, 1977, pp. 229-233, vol. 28; Pergamon Press.
H.F. Kung et al., A New Myocardial Imaging Agent: Synthesis, Characterization, and Biodistribution of Gallium-68-BAT TECH, *The Journal of Nuclear Medicine*, 1990, pp. 1635-1640, vol. 31, No. 10.
Jaetae Lee et al., "In Vitro and In Vivo Evaluation of Structure-Stability Relationship of $^{111}$In- and $^{67}$Ga-Labeled Antibody via 1B4M or C-NOTA Chelates," *Nuclear Medicine and Biology*, 1997, pp. 225-230, vol. 24, Elsevier Science.
R.E. Lewis et al., Germanium-68/Gallium-68 Generator for the One Step Elution of Ionic Gallium-68, *Journal of Labelled Compounds & Radiopharmaceuticals*, 1981, 164, vol. XVIII, Nos. 1-2.

(Continued)

*Primary Examiner*—Dameron L. Jones
(74) *Attorney, Agent, or Firm*—Heller Ehrman LLP (57) ABSTRACT

A method and compositions are described for labeling a targeting agent with Ga-68, in which eluate from an acid-eluted Ge-68/Ga-68 generator is combined with a macrocycle-containing targetable agent. The labeling method and compositions disclosed ensure that a simple elution of gallium-68, taken directly from a generator, can be used without further manipulation to quantitatively label a macrocycle-containing targetable agent. The Ga-68 labeled targeting agent so produced is useful with specific targeting agents, and is most especially useful in a pretargeting method for positron emission tomographic detection.

36 Claims, 1 Drawing Sheet

OTHER PUBLICATIONS

C. Loc'h et al., "A New Generator for Ionic Gallium-68," *Nuclear Medicine*, 1980, pp. 171-173, vol. 21, No. 2.

Karen D. Mcelvany et al., "Comparison of $^{68}$Ge/$^{68}$Ga Generator Systems for Radiopharmaceutical Production," *The International Journal of Applied Radiation and Isotopes*, 1984, pp. 521-524, vol. 35, No. 6.

R.D. Neirinckx et al., "Potential Column Chromatography for Ionic Ga-68. II: Organic Ion Exhangers as Chromatographic Supports," *Journal of Nuclear Medicine*, 1980, pp. 81-83, vol. 21, No. 1.

Jochen Schuhmacher et al., "Multistep Tumor Targeting in Nude Mice Using Bispecific Antibodies and a Gallium Chelate Suitable for Immunoscintigraphy with Positron Emission Tomography[1]," *Cancer Research*, 1995, pp. 115-123, vol. 55, No. 1.

Yizhen Sun et al., "Indium (III) and Gallium (III) complexes of Bis(aminoethanethiol) Ligands with Different Denticities: Stabilities, Molecular Modeling, and in Vivo Behavior," *Journal of Medical Chemistry*, 1996, pp. 458-470, vol. 39, No. 2.

Chuanchu Wu et al., "Biodistribution and Catabolism of Ga-67-Labeled Anti-Tac dsFv Fragment," *Bioconjugate Chem.*, 1997, pp. 365-369, vol. 8, No. 3.

Brenda W. Tsang, et al., "A Gallium-68 Radiopharmaceutical That is Retained in Myocardium: $^{68}$Ga[(4,6-MeO$_2$sal)$_2$BAPEN]$^+$," *The Journal of Nuclear Medicine*, 1993, pp. 1127-1131, vol. 34, No. 7.

Table of Contents, *Journal of Nuclear Medicine*, vol. 2, No. 1, Jan. 1961, Eighth Annual Meeting, Pennsylvania.

M.A. Gracheva, et al., The Reaction Mechanism of the Technetium 99-m Complex Formation with the Ligands used for the Preparation of Radiopharmaceutical Medicines, *Journal of Labelled Compounds & Radiopharmaceuticals*, 1982, pp. 1535-1536, vol. XIX, Nos. 11-12.

Hsu, et al., "Cutting Edge: BLyS Enables Survival of Transitional and Mature B Cells Through Distinct Mediators", The Journal of Immunology, pp. 5993-5998 (2002).

\* cited by examiner

Figure 1.

LABELING TARGETING AGENTS WITH GALLIUM-68 AND GALLIUM-67

CROSS-REFERENCE TO RELATED APPLICATIONS

This application claims priority from U.S. Provisional Serial No. 60/342,104, filed Dec. 26, 2001, which is incorporated herein in

STATEMENT REGARDING FEDERALLY SPONSORED RESEARCH OR DEVELOPMENT

Part of the work performed during development of this invention utilized U.S. Government funds. The U.S. Government has certain rights in this invention. Part of the work described in this invention was supported by a PHS grant 1R43 CA-83424-01from the National Institutes of Health.

FIELD OF THE INVENTION

The present invention relates to improved methods for labeling targeting agents, particularly with Ga-68, and the labeled targeting agents produced thereby, as well as their uses.

BACKGROUND OF THE INVENTION

Specific targeting agents bearing a detectable moiety offer the potential for earlier diagnosis of disease, if an increased amount of the targeting-detectable conjugate is localized to a greater extent in tissue to be imaged compared to background tissues. In practice, detectable agent in background tissue needs to be minimized while detectable agent in target tissue needs to be maximized. Radioactive nuclides are preferred detectable agents and nuclides such as Tc-99m and In-111 are widely used for scintigraphy and single photon emission computed tomography. However, there are limitations on the sensitivity of these detection modalities. For instance, even for specific targeting of tumor tissue in a patient, tumor nodules of less than 1 centimeter diameter may be very difficult to detect. A superior imaging modality is offered by positron emission tomography (PET), which offers the promise of a dramatic increase in sensitivity, and therefore the ability to detect disease at an earlier stage. What has mainly hampered development of PET into a routinely applied clinical diagnostic modality are the inadequate techniques related to radiolabeling of specific targeting agents with useful PET nuclides.

There are about 20 nuclides of theoretical utility for PET in that they have positron decay and a suitable half-life (minutes or longer). In practice, most of these nuclides are really unsuitable for a variety of reasons, including, several separate reasons in the case of many of them. These reasons include but are not limited to, availability and cost of parent nuclides, nuclide preparation issues related to target preparation and bombardment, handling and shipment of the nuclide, cyclotron size and energy etc., chemical separation issues, radiolabeling issues including on-site radiolabeling issues, and decay energy and properties of the PET nuclides themselves which often include other beta and/or gamma decay. These extensive and severe practical matters can essentially preclude most nuclides from consideration as viable PET agents, and the two most commonly considered nuclides for PET, fluorine-18 and gallium-68, retain the best combination of features, and fewest problems among PET nuclides. Gallium-68 (Ga-68) has two great advantages over F-18 when considering both nuclides for PET usage. First, it is available from a generator, which makes it available on site by a simple 'milking' process that can be carried out daily, or even hourly. This makes Ga-68 independent of the need for a nearby cyclotron, as is needed for F-18. Second, it is a radiometal and can be complexed by suitable chelating agents. In contradistinction, fluorine is mainly available as F-18 fluoride ion in aqueous solution and this must be taken into a dry organic environment prior to chemical manipulations to covalently attach it to targeting agents of choice. The half-lives of both nuclides are short (F-18~2 h; Ga-68~68 minutes) and the intense positron energy emitted makes chemical manipulations far from trivial and possibly extremely hazardous to technical personnel. Given the chemistry needed for F-18 attachment to targeting agents, the radiochemical processes can only be carried out in custom-designed dedicated facilities, and these facilities must also be located near a cyclotron that produces the F-18 raw material.

Gallium-68 does not suffer from these drawbacks. It is available from a long-lived parent nuclide (germanium-68; half-life 288 days) that can be adsorbed to various solid phases, from which the Ga-68 can then be selectively eluted. Thus, a Ga-68 generator can be fabricated, and several have been described (Ambe, 1988; Greene and Tucker, 1961; Loc'h, 1980; Lewis 1981; Hanrahan, 1982; McElvaney, 1983; Neirinckx, 1980). The most developed generator is one based on adsorption of the parent Ge-68 to a stannic oxide bed (Loc'h, 1980), from which the Ga-68 is eluted with dilute hydrochloric acid. Alternate generators have utilized alumina as adsorbent and EDTA to elute the gallium-68, which presents significant problems in conversion of Ga-68-EDTA complex to other species, given the 68-minute half-life of the nuclide. The invention described herein is preferably directed toward generators of the first type that can be eluted with acid or salt solutions, rather than with chelates such as EDTA.

Given the availability of Ga-68 generators over many years, it is very surprising that no Ga-68-labeled targeting agents have been developed past the point of research article material, and toward routine clinical use. It is one object of the present invention to overcome the radiolabeling problems that have prevented routine clinical preparation of Ga-68-labeled targeting agents.

Gallium is an amphoteric element, which is to say that it displays both basic and acidic reactive properties, and this considerably complicates manipulation of radiogallium. In addition, in dilute solution gallium tends to form non- or poorly-chelated chemical species. The short-lived Ga-68 eluted carrier-free from a generator is present in extremely dilute solution, typically under one picomole ($10^{-12}$ moles) per milliCurie. It can therefore be particularly prone to the formation of gallates and other species (Hnatowich, 1975; Kulprathipanja and Hnatowich, 1977). This is particularly so as the pH is raised and hydroxy or aqua-ions tend to replace chloride ions in the immediate vicinity of the gallium ions.

Ge-68/Ga-68 generators of the stannous oxide type are usually eluted with a 10–12 mL portion of ultra-pure 1 N hydrochloric acid, providing the Ga-68 daughter in highly dilute form and in the presence of a large amount of hydrochloric acid. Without a purification step, there is also the possibility of eluting other extraneous metal ions along with the Ga-68, and each of these, even in nanomolar amounts, would be typically in 100–10,000 molar excess to the Ga-68. Anionic stannates, can also be eluted which can also complicate carrier-free radiolabeling methods. Once the Ga-68 is obtained, there is then a challenge to bind it to a targeting species, in light of all the above potential problems, and this has been approached in several distinct ways.

First, some workers decided that the carrier-free Ga-68 needed to be mixed with cold gallium to prevent problems seen at high dilution, and so cold gallium was added to Ga-68 eluate prior to admixing with the material to be Ga-68 radiolabeled (Schuhmacher, 1995; Klivényi, 1998). This is cumbersome, and also precludes the preparation of high specific activity Ga-68-labeled species, since the cold added gallium must also be bound by any chelate added during labeling.

A second approach relied on the use of the 'transchelator' acetylacetone (2,4-pentanedione) in large excess to bind to radiogallium, essentially using it to out-compete the hydroxy/aqua ions present in the aqueous solution (Lee, 1997; Wu 1997). Unfortunately, this approach is not useful clinically since acetylacetone is a neurological toxin, teratogen and possible mutagen.

A third approach described the evaporation of the Ga-68 eluate from the generator to dryness under a flow of inert gas (Sun, 1996). This was done to remove the excess HCl and to allow the reconstitution of the Ga-68 in another medium. One variation of the method also called for the addition of acetylacetone to protect the Ga-68 while the drying process was continuing (Green, 1993; Tsang, 1993).

Finally, a fourth approach recommended addition of extra concentrated HCl to the Ga-68 generator eluate, until the HCl was 6 N in concentration (Kung, 1990). Then, the Ga-68 in concentrated HCl, was extracted with diethyl ether and reduced to dryness under a stream of nitrogen.

The most advanced technology for clinical application and use of Ga-68 was developed over a three year period, and was based on the evaporation of a reduced elution volume of Ga-68 eluate in 1 N HCl (Goodwin, 1994). Prior to evaporation the Ga-68 was eluted from the Ge-68/Ga-68 generator through an AG1X8 ion exchange filter, and then evaporated on a rotary evaporator, prior to being reconstituted in 10 mM HCl.

Use of Ga-68 carries with it the following concerns: 1) The Ga-68 has a half-life of only 68 minutes, and therefore any methodology used should be fast. 2) Danger to technical personnel is high since the Ga-68 nuclide decays with positron emission at 511 keV making the emergent gamma-rays very difficult to block even with thick (>one inch) lead shielding. 3) In a clinical scenario, the Ga-68 must be obtained sterile and pyrogen-free, and this along with 2) above creates a preference for a method in which manipulations are kept to a minimum. 4) Clinical technical staff have limited chemistry expertise, and are under constant time pressure to produce other unrelated agents during a normal day. They cannot be expected to perform intricate manipulations of the above types in order to effect a Ga-68 labeling.

The above summary of work over a 20-year or so period clearly indicates a need in the art for a viable, rapid and simple method for Ga-68 labeling of specific targeting agents. Disadvantages in the previous methods of Ga-68 labeling have prevented routine adoption of the acid-eluted Ge-68/Ge-68 generators in clinical PET, and have subsisted for over 20 years.

SUMMARY OF THE INVENTION

It is an object of the invention to provide a Ga-68 labeling method (also useful with gallium-67) that is fast, safe and does not require complicated chemical manipulations, along with compositions useful in the practice of the method. Development of such a new methodology enables the wider use of Ge-68/Ga-68 in-house generators, which have not been widely used before due to both the inherent difficulties in handling gallium-68, and the difficulties in producing useful imaging agents containing gallium-68 in a reasonable time-frame while using only simple methodologies. In turn, the present invention while allowing the ready use of Ga-68 eluate in a clinical setting, will lead to the greater adoption of PET-based procedures for identification of diseases, and thereby, the earlier and more accurate detection of said diseases. Again, in turn, this should lead to better to better treatment options and greater cure rates.

In one aspect, the invention combines a method of eluting, with an acidic solution, a stannic oxide or titanium dioxide based, or similar, Ge-68/Ga-68 generator. The gallium-68 is eluted such that the entire available yield of Ga-68 is passed directly into a vial containing a solution or a lyophilized preparation of the chelate-targeting agent conjugate that is to be labeled. Using the methods and compositions of this invention it is now possible to effect an approximately 80–100% incorporation of Ga-68 into a chelate-targeting agent conjugate, such that the labeled material can be used, optionally, without further purification procedures. The chelate-targeting agent conjugate can be compounded into kits, formulated, stabilized and ready-to-use, to accept the Ga-68 from the generator, as eluted in acidic solution.

Another embodiment of the invention is a composition comprising a targeting agent labeled with Ga-68; wherein said Ga-68 associates with a chelate-containing conjugate comprising a macrocyclic ring. Such macrocyclic rings are exemplified by 1,4,7-triazacyclononane-N,N',N"-triacetic acid (NOTA) and 1,4,7,10-tetraazacyclododecane-N,N', N",N"'-tetraacetic acid. Such macrocyclic ring moieties are linked to a useful targeting agent, for example a peptide that can target a site of disease, either directly or indirectly. The gallium-68 compositions thus formed may be used in positron emission tomographic detection methods (with or without preceding, concomitant, or subsequent therapy). An example of a useful disease specific targeting method, wherein the current compositions and methods invention find application is as agents useful in pre-targeting methods for positron emission tomographic detection (with or without preceding, concomitant, or subsequent therapy). In this embodiment, a multi-specific targeting agent having at least one binding site for a hapten and at least one binding site for a diseased tissue is administered to a mammalian patient in need thereof. Once this multi-specific targeting agent has maximized its accumulation at the site of disease and its levels in non-target tissues and circulation have dropped to an acceptably low level, the composition containing the gallium-68 imaging nuclide is given. The patient and his/her disease may then be imaged using positron emission tomography at times from 15 minutes to eight hours post-administration of the gallium-68-containing hapten. The general method of this 'pretargeting' embodiment is described in U.S. Pat. No. 5,256,395 (Barbet et al., 1993).

Another embodiment is a composition comprising a macrocyclic-targeting agent conjugate dissolved in sufficient pH-neutral buffer to enable substantially complete incorporation of Ga-68 when admixed with a solution of Ga-68 in dilute acid. Such buffers are exemplified by relatively concentrated solutions (0.1 to 5 M) of acetate salts at pH 5–8. Another embodiment comprises a kit containing sufficient macrocyclic chelate-conjugated targeting agent together with sufficient ammonium acetate buffer to bind an added acidic Ga-68 solution. The kit of the invention is formulated such that sufficient neutralizing buffer, e.g. ammonium acetate, is present to substantially neutralize the excess acid in which the Ga-68 is added, allowing facile complexation by of the added Ga-68 by the macrocyclic chelate-conjugated targeting agent.

buffer of appropriate concentration into which Ga-68 in 0.5 to 1 normal hydrochloric acid generator eluent is eluted directly.

Formula I. Structure of the peptide termed IMP 244.

DETAILED DESCRIPTION OF THE PREFERRED EMBODIMENTS

Unless otherwise specified, the terms "a" or "an" mean "one or more".

Any chelate to be used within this invention must be capable of binding Ga-68, preferably in very dilute solution, quickly, near quantita irreversibly over a 1–4 h period. Preferred chelates of the invention are exemplified by macrocyclic derivatives such as "NOTA", which is [1,4,7-triazacyclononane-N,N',N"-triacetic acid] or "DOTA'[1,4,7,10-tetraazacyclododecane-N,N',N",N'"-tetraacetic acid]. A preferred peptide bearing a NOTA residue, and that is useful in specific targeting is shown in Formula I. It has the Immunomedics code number IMP 244. Specific targeting is effected by use of a multi-specific pret bispecific monoclonal antibody that recognizes with at least one arm a tumor-associated antigen, and with at least one other arm a hapten. In this case, the hapten is represented by the substituent termed HSG, for a histaminyl-succinyl-glycyl- moiety (Formula II). An example of such a bispecific antibody would be hMN-14×679-F(ab')₂, wherein hMN-14 represents a humanized Fab' arm of an anti-carcinoembryonic antigen (anti-CEA) antibody, and 679 represents a Fab' arm of an antibody raised against the HSG hapten.

A preferred peptide bearing a DOTA residue, and that is useful in bispecific antibody pretargeting methodology is IMP 241, and is shown in Formulae III. Similarly to IMP 244, it comprises a tetrapeptide backbone substituted with two HSG sub-units, but in this case carries the DOTA macrocyclic chelate. In this example, the DOTA chelate is linked to the amino-terminal alpha amino acid residue (in this example phenylalanine) via one of its carboxyl groups, whereas the NOTA macrocycle of IMP 244 is linked to its peptide backbone via a discrete isothiocyanato-benzyl group attached to a single carbon on the macrocyclic ring. For the purposes of the current invention the manner of the coupling of the macrocyclic chelate to the peptide backbone carrier, is not important, as long as said macrocyclic chelate, once conjugated, can still bind gallium.

Particular solutions of the above, and similar, peptides can be prepared such that a tin oxide- or titanium dioxide-based Ge-68/Ga-68 generator can be diluted directly into such solutions to effect a facile Ga-68 labeling and produce an agent that requires no further purification prior to use. Useful peptidyl solutions are prepared in an appropriate buffer, useful in the pH 2–6 range, such as an ammonium acetate Formula II. Structure of the histaminyl-succinyl-glycyl (HSG) sub-unit moiety.

Formulae III. Structures of the histaminyl-succinyl-glycyl (HSG) sub-unit moiety, the DOTA sub-unit moiety and the peptide incorporating the di-HSG and mono-DOTA sub-units, termed IMP 241.

IMP 241: DOTA-Phe-Lys(HSG)-D-Tyr-Lys(HSG)-NH2

Histamine-succinyl-glycyl-
[HSG]

In a detailed example, NOTA-containing peptide IMP 244 is dissolved in 2 mL of 4M-ammonium acetate buffer, pH 7.2. The Ge-68/Ga-68 generator is eluted with a reduced amount of hydrochloric acid (HCl) from that recommended by the manufacturer, in this case a $SnO_2$-based generator (NEN, Billerica, Mass.). Typically, this elution volume can be 2–5 mL instead of 20 mL recommended by this particular manufacturer. The lesser amount can be used without significant loss of recovered activity, by judicious selection of the central portion of the elution peak. The Ge-68/Ga-68 generator may be optionally fitted with an anion-exchange membrane such as a Q5F cartridge (Sartorius AG, Goettingen, Germany), to remove any eluted stannate packing material that may be eluted from the generator with the HCl. The HCl used is of the purest form available (e.g. Optima grade HCl from Fisher Scientific, Pittsburgh, Pa., diluted down to a concentration of 0.5–1.0 N using 18 MegOhm purity deionized water.) to assist in maintaining Ga-68 yield without introducing the contaminating effect of other metals. The generator can be eluted with 1N HCl, or with similarly good recovery of expected Ga-68, with 0.5 N HCl. The pH of the final labeling mixture is typically between 4.5–4.8, depending upon whether 1 N or 0.5 N HCl has been used for generator elution.

The amount of NOTA-peptide, IMP 244, needed to effect satisfactory labeling within a 30 minute to 1 h time frame is generally above $1 \times 10^{-9}$ moles, more preferably above $1 \times 10^{-8}$ moles, and most preferably at or above $5 \times 10^{-8}$ moles. Since, in this instance, the final volume is approximately 7 mL of combined generator eluate and ammonium acetate buffer, the lowest molarity of NOTA-peptide needed for effective labeling is in the range of 1–10 micromolar. A preferred labeling temperature is somewhat elevated, from ambient into the 35–45° C. range. Labeling can also be accomplished at more elevated temperatures, for example at 60–100 degrees Celsius.

In an embodiment using the IMP 241 peptide, the DOTA-peptide is placed in a [preferably] acid-washed glass, plastic or resin vial. Around $1.0 \times 10^{-7}$ to $1.0 \times 10^{-9}$ moles of the DOTA-peptide is a most preferred amount, although somewhat lesser or greater amounts may also be successfully used. This amount of peptide is generally then mixed with approximately 1–2 mL of 2–5 M ammonium acetate buffer, pH 5.0 to pH 8.0. The composition may then be stored at four degrees, frozen or lyophilized for future use, or it may be used immediately. Such formulations can be prepared in multiple sealed vials, and made under sterile, pyrogen-free conditions for manufacturing and general use purposes.

For gallium-68 radiolabeling, an IMP 241 composition prepared according to the above description is placed onto the outlet valve of a germanium-68/gallium-68 generator. The vial containing the peptide is shielded in lead, preferably 1–2 inches thick. By use of plastic tubing the operator then elutes the generator with dilute hydrochloric acid from a remote position into the shielded vial of the DOTA-peptide composition. Generally, the generator can be eluted using a hand pushed syringe containing the acid, or it can be conveniently eluted using a peristaltic pump. The elution time is advantageously kept under 15 minutes, more preferably under five minutes, given the 68-minute half-life of the gallium-68 radionuclide. A needle or catheter, which can be metallic, but is preferably non-metallic, is used to maintain equal pressure inside and outside of the vial during the elution.

The Gallium-68 generator is eluted with between 1 and 10 mL of hydrochloric acid, preferably 2–5 mL, to ensure adequate yield of the gallium-68 into the collection vial, without unwanted over-dilution. The acid used is preferably of the highest purity possible in order to maintain good recovered yield of gallium-68 over an extended time period, to maximize utility of the generator. During elution, the first several mL of generator eluent may be diverted to waste, before the main fraction containing the gallium-68 is harvested. The vial of IMP 241 is then heated at 95° C., with lead shielding, in a water-bath for 15 minutes. Gallium-68 radiolabelings can also be done in as little as five minutes, or can take up to an hour and still be useful, with conditions also being particularly dependent on the amount of peptide used in the formulation and the final pH of the labeling mixture. The preferred final pH is between 2 and 6, with the most preferred pH being between 3 and 5.

Any macrocyclic chelate-peptide conjugate can be labeled using the above simplified techniques, and specific targeting agents such as octreotide, LHRH, somatostatin and gastrin, if bearing a macrocyclic chelate such as NOTA or DOTA can be used in the invention. In a preferred embodiment, peptides such as IMP 244 and IMP 241, herein disclosed, are usefully labeled with Ga-68 and are then used as Ga-68 complexes within pretargeting methods for Ga-68 PET imaging. The pretargeting method combines the use of a primary disease targeting agent that is multispecific for both disease and a user-defined hapten, with the use of a later-administered hapten labeled with an imaging or therapy agent; in this instance with gallium-68. Preferably, the user-defined hapten is bivalent for the multispecific targeting agent, and is able to cross-link the former specifically at disease sites, producing an 'affinity enhancement effect'.

The hapten is designed by the user for its utility is several aspects. Most importantly, the hapten is designed to clear living systems very rapidly. It is preferably very hydrophilic, even when bearing gallium. Exemplified in this disclosure are the examples of the peptides IMP 244 and 241, both bearing two HSG sub-units, used for recognition by an anti-HSG antibody arm (termed 679). The HSG sub-units also impart hydrophilicity on the final hapten structure besides being integral to the binding process. However, it must be understood that other sub-unit recognition units and other backbone sub-units could be just as easily used within the scope of the invention. For the latter, peptides are useful, and any sequence could be designed using standard methods of peptide syntheses. Other backbone sub-units, such as sugars and dextrans are also contemplated as within the scope of the current invention.

Heretofore it had been disclosed that use of a germanium-68/gallium-68 generator involved post-elution manipulation of the eluted gallium-68, to concentrate the nuclide and keep it in a chelatable form. These procedures involved organic solvent-from-acid extractions, low-pressure evaporations and other detailed hands-on techniques as outlined in the background above. It must be understood that a commercially viable and clinically acceptable method for adoption of gallium-68-labeled imaging agents for PET is incompatible with all these previously described, complex radiolabeling methods. This is true for multiple reasons, most importantly because of the extreme hazards in handling the high-energy, high intensity Ga-68 (positron energy 1900 MeV), and the need to maintain sterility and apyrogenicity while working with the 68-minute half-life gallium-68. The invention, in its entirety and unlike previous art, represents a very simple integrated process for performing facile labeling of macrocycle-(NOTA- and DOTA)-containing, disease-targeting conjugates with gallium-68. The present invention is further illustrated by, though in no way limited to, the following examples.

EXAMPLES

Example 1

Acid Elution of a Ge-68/Ga-68 Generator

A Ge-68/Ga-68 generator is placed inside a half-inch lead 'molycoddle' for extra shielding, and this is further surrounded by a 2-inch thick lead wall. The inlet of the generator is fitted with sterile tubing and a 3-way stopcock. The two other ports of the stopcock are attached to a 10-mL sterile syringe and a source of ultra-pure 0.5 N hydrochloric acid, respectively. The outlet port of the generator is fitted with sterile tubing and a QF5 anion exchange membrane that had been previously washed with 0.5 N hydrochloric acid. By means of the inlet syringe, a 5-mL portion of the 0.5 N hydrochloric acid is withdrawn from the stock solution, the stopcock is switched to allow access to the generator column, and the acid is hand-pushed through the generator. The eluate containing the Ga-68 is collected in a lead-shielded acid-washed vial optionally already containing the NOTA-containing targeting agent to be Ga-68 radiolabeled.

Example 2

Ga-68 Labeling of IMP 244 Peptide Using the Above Elution Technique

A $5 \times 10^{-8}$ portion of the NOTA-containing peptide IMP 244 is mixed with 2 mL of 4M metal-free ammonium acetate buffer, pH 7.2, in an acid-washed vial. The Ga-68 ingrowth from the generator, 5 mCi, is eluted dire the techniques described in the previous example. After brief mixing, the vial contents are heated 30 minutes at 45° C. The incorporation of Ga-68 into the IMP 244 is measured at 94%, after the 30-minute labeling time, by size-exclusion high-performance liquid chromatography (SE-HPLC) on a Bio-Sil 250 column run in 0.2 M phosphate buffer, pH 6.8, with column recovery determined, and detection by in-line Radiomatic detection using energy windows set for Ga-68. Corroborative data is obtained using instant thin-layer chromatography (ITLC) using silica gel-impregnated glass fiber strips (Gelman Sciences, Ann Arbor, Mich.), developed in a 5:3:1 mixture of pyridine, acetic acid and water.

Example 3

Ga-68-IMP 244 and anti-HSG MAb Complex Formation

An aliquot of the Ga-68-IMP 244 complex is mixed with a 20-fold molar excess of bispecific antibody (bsAb) hMN-14×679 F(ab')$_2$ [anti-CEA×anti-HSG] in 0.2 M phosphate buffered saline, pH 7.2, and reapplied to the above SE-HPLC analytical system. The radioactivity that eluted at a retention time of around 14.2 minutes in the last example was near-quantitatively shifted to a retention time near 8.8 minutes after mixing with the bispecific antibody. Comparison to this retention time to those from application of molecular weight standards to the SE-HPLC under the same conditions indicate that the radioactivity has shifted to a molecular weight near 200,000 Daltons.

Example 4

Stability Studies on the Ga-68-IMP 244 Peptide a) To EDTA: The Ga-68-IMP 244 peptide is diluted into 0.2M sodium phosphate buffer containing 1 mM EDTA and allowed to stand at room temperature. At periods up to 2–3 h post-incubation aliquots were tested by size-exclusion high-performance liquid chromatography in the above system. In this system, Ga-68-IMP 244 elutes near 14.2 minutes, while Ga-68-EDTA elutes near 13.7 minutes. Upon further mixing of an aliquot of the Ga-68-IMP 244+EDTA mixture with a 20:1 molar excess of hMN-14×679 F(ab')$_2$ bisAb and re-analysis by SE-HPLC, the radioactivity peak that eluted at a retention time of around 14.2 minutes was near-quantitatively shifted to a retention time near 8.8 minutes, showing that the Ga-68-IMP 244 is stable to EDTA challenge over a multi-hour period.

b) In Human Serum: A 100-uL sample of the Ga-68-IMP 244 is mixed with 2 mL of whole human serum and incubated over a 3 h period at 37° C. Aliquots are taken at intermediate times and analyzed by SE-HPLC. No change in retention time from the original 14.2 minutes corresponding to Ga-68-IMP 244 is seen, proving no non-specific binding to any of the components that comprise human serum, and no loss of radioactivity from Ga-68-IMP 244 to any of the components that comprise human serum. Additionally, after 3h incubation, upon further mixing of an aliquot of the Ga-68-IMP 244 in human serum mixture with a 20:1 molar excess of hMN-14×679 F(ab')$_2$ bsAb and re-analysis by SE-HPLC, the radioactivity peak that eluted at a retention time of around 14.2 minutes was near-quantitatively shifted to a retention time near 8.8 minutes. This shows that the Ga-68 remains bound to the IMP 244 peptide, and the latter is still functionally able to bind to the hMN-14×679 F(ab')$_2$ bsAb.

Example 5

Preparation of Ga-68-IMP 241

Figure 1:
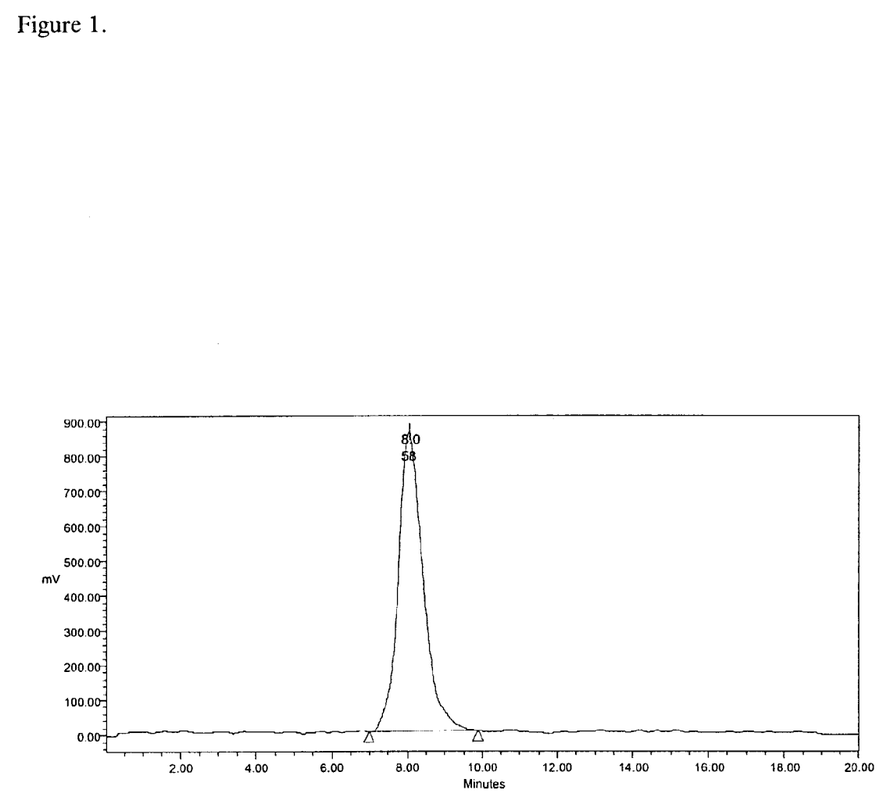
FIG. 1 is a typical size-exclusion HPLC trace of the complex 679-IgG (anti-HSG) admixed with the radiolabeled peptide Ga-68-IMP 241. The y-axis plots radioactivity against time (x-axis). All recovered Ga-68 elutes as the complex between the antibody and the Ga-68-labeled peptide, near 8 minutes retention time, at an apparent molecular weight of approximately 160,000 Daltons. Free Ga-68 peptide would elute at around 14 minutes retention time.

In an acid washed 10 mL CZ-Resin vial (West Pharmaceutical Services #19550022) are mixed 1.0 mL of 2.5M NH$_4$OAc, pH 5.5 buffer, and 11.4 uL of a stock solution of $2.2 \times 10^{-3}$ M IMP 241 in 0.5M NH$_4$OAc, pH 4, ($2.5 \times 10^{-8}$ mol of total peptide). The vial is stoppered with an acid washed Flurotec stopper (West Pharmaceutical Services #1243), crimped closed and swirled to mix thoroughly. The Gallium-68 generator is then eluted with 6 mL 1N HCl (OPTIMA Fisher #A466-250, diluted to 1N with 18 MegOhm water), with the first two mL of generator eluent diverted to waste. With a vent needle (18G 1¼" Jelco i.v. Catheter Placement Unit, (VWR #32918-880) in place, the generator eluent is directed into the labeling vial through a non-metallic catheter. The vial is then heated at 95° C. in a water-bath for 15 minutes. The final pH of the labeling mixture is approximately 3.9. For radioanalysis, an aliquot is withdrawn and diluted to 0.05 uCi/uL with sterile saline. Ten-twelve uL of the dilution (containing approximately 0.5–0.6 uCi of Ga-68) is mixed with a 20-fold molar excess m679-IgG anti-HSG antibody and applied to a size-exclusion Bio-Sil- Sec-250 column equilibrated and run in 0.2M sodium phosphate buffer, pH 6.8, containing 0.02% sodium azide, at 1 mL/minute. Column recovery of applied radioactivity is done by collecting the entire eluent from the 20-minute run and counting 3×1 mL aliquots therefrom against 3×1 mL aliquots of a standard prepared by diluting the same volume of labeled peptide in 20 mL HPLC column elution buffer. SE-HPLC Column recovery upon successful radiolabeling is>80%. An example of the radio-HPLC analysis of the Ga-68-IMP 241–679 IgG MAb complex is shown in FIG. 1.

Example 6

Specific Localization of Ga-67-IMP 241 Using Bispecific Antibody Pretargeting:

Gallium-67 was used in lieu of gallium-68 due to the 68-minute half-life of the latter, and the inherent difficulties of quantitating the activity of gallium-68 in tissue due to significant reduction in radioactivity during the counting period. The bispecific antibody I-125-hMN-14×679-F(ab')$_2$ (anti-CEA×anti-HSG, radiolabeled with iodine-125 as a tracer radionuclide) was injected into nude mice bearing GW39 human colon tumor xenografts. Twenty-four hours later, the Ga-67-IMP 241 peptide, prepared according to the method described in Example # 4, was injected. At specified times post-injection, five animals per time-point were sacrificed and tissues collected and counted for both I-125 and Ga-67 radioactivity, using dual energy windows for each respective radionuclide. Data for I-125 (bsAb) is shown in Table 1, and data for Ga-67 (IMP 241) is shown in Table 2. Additionally, biodistribution of Ga-67-IMP 241 given alone, without bsAb pretargeting is shown in Table 3 (four animals per group in this series). In each Table, the data is presented in terms of percent injected dose per gram of tissue (± standard deviation). Additionally, the biodistribution data for I-125-hMN-14×679-F(ab')$_2$ and Ga-67-IMP 241, from the same experiment, is reported in terms of tumor-to non-tumor ratio (T/NT) (Tables 4 & 5, for 1–125 and Ga-67, respectively).

The uptake of the peptide mirrors uptake of bsAb in almost all tissues (Table 1 & 2). Tumor-to-tissue ratios for the Ga-67-IMP 241 are better at later time-points, apparently without any significant loss of Ga-67 counts in the target tumor. When the Ga-67-IMP 241 is given alone (Table 3), it essentially clears completely within the first hour post-injection, with no non-specific uptake in any tissue save residual kidney activity, proving that the Ga-67-DOTA complex on the IMP 241 peptide is stable enough for use with Ga-68. T/NT ratios are positive for the I-125-hMN-14×679-F(ab')$_2$ from the earliest (one hour time-point measured) (Table 4), with stomach the lowest positive ratio, due to normal clearance of antibody-cleaved radioiodine in that organ. Most importantly, the data in Table 5 shows T/NT ratios for the prospective imaging agent analog at major time-points of interest. By two hours, the mean ratio is above 6:1 for tumor-to-blood, and is very high for all other tissues, even ~3.5:1 for tumor-to-kidney, meaning that excellent images will be obtainable by this time. In fact, strongly positive tumor-to-non-tumor ratios are seen for all organs from one hour post-injection onwards, proving that this imaging system will be useful for PET with the 68-minute half-life gallium-68.

TABLE 1

Biodistribution of I-125-hMN-14 × 679-F(ab')$_2$ bispecific antibody. Data in terms of percent injected dose per gram of tissue (±standard deviation).

| Tissue | Times are post-injection of peptide (+24 h post-injection of bsAb) | | | | |
|---|---|---|---|---|---|
|  | 1 h | 2 h | 3 h | 4 h | 6 h |
| Tumor | 3.1 ± 1.0 | 2.4 ± 0.9 | 1.5 ± 0.6 | 2.5 ± 0.9 | 2.5 ± 1.2 |
| Liver | 0.7 ± 0.1 | 0.4 ± 0.1 | 0.5 ± 0.2 | 0.4 ± 0.1 | 0.5 ± 0.1 |
| Spleen | 1.0 ± 0.4 | 0.6 ± 0.4 | 0.6 ± 0.1 | 0.6 ± 0.3 | 0.7 ± 0.3 |
| Kidney | 0.7 ± 0.1 | 0.5 ± 0.1 | 0.5 ± 0.1 | 0.4 ± 0.1 | 0.4 ± 0.1 |
| Lungs | 0.8 ± 0.3 | 0.4 ± 0.1 | 0.4 ± 0.1 | 0.4 ± 0.1 | 0.5 ± 0.1 |
| Blood | 1.5 ± 0.2 | 1.0 ± 0.3 | 0.8 ± 0.2 | 0.9 ± 0.2 | 1.0 ± 0.3 |
| Stomach | 2.9 ± 0.7 | 1.3 ± 1.0 | 1.6 ± 1.2 | 1.5 ± 1.1 | 2.4 ± 1.8 |
| Sm. Intestine | 0.3 ± 0.1 | 0.2 ± 0.1 | 0.2 ± 0.1 | 0.2 ± 0.1 | 0.2 ± 0.1 |
| Lg. Intestine | 0.3 ± 0.0 | 0.3 ± 0.1 | 0.3 ± 0.1 | 0.3 ± 0.1 | 0.3 ± 0.2 |
| Bone | 0.5 ± 0.1 | 0.2 ± 0.1 | 0.3 ± 0.1 | 0.2 ± 0.1 | 0.2 ± 0.1 |

TABLE 2

Biodistribution of Ga-67-IMP 241 given 24 hours after I-125-hMN-14 × 679-F(ab')$_2$ bispecific antibody. Data in terms of percent injected dose per gram of tissue (±standard deviation).

| Tissue | Time post-injection of Ga-67-IMP 241 peptide | | | | |
|---|---|---|---|---|---|
|  | 1 h | 2 h | 3 h | 4 h | 6 h |
| Tumor | 13.2 ± 5.8 | 10.7 ± 6.7 | 8.3 ± 6.1 | 11.7 ± 4.8 | 16.0 ± 8.7 |
| Liver | 1.7 ± 0.4 | 0.7 ± 0.3 | 0.8 ± 0.3 | 0.9 ± 0.6 | 1.0 ± 0.5 |
| Spleen | 1.4 ± 0.5 | 0.6 ± 0.5 | 0.6 ± 0.2 | 0.8 ± 0.6 | 1.0 ± 0.5 |
| Kidney | 6.3 ± 1.5 | 3.1 ± 1.3 | 3.4 ± 0.3 | 3.8 ± 0.8 | 3.7 ± 1.5 |
| Lungs | 2.9 ± 0.9 | 0.9 ± 0.5 | 0.8 ± 0.2 | 1.0 ± 0.6 | 0.8 ± 0.3 |
| Blood | 8.2 ± 1.8 | 2.1 ± 1.6 | 1.3 ± 0.5 | 1.7 ± 1.2 | 1.4 ± 0.6 |
| Stomach | 0.4 ± 0.2 | 0.2 ± 0.1 | 0.1 ± 0.0 | 0.4 ± 0.6 | 0.1 ± 0.1 |
| Sm. Intestine | 0.7 ± 0.1 | 0.4 ± 0.3 | 0.2 ± 0.0 | 0.7 ± 0.6 | 0.5 ± 0.4 |
| Lg. Intestine | 0.2 ± 0.1 | 0.2 ± 0.1 | 0.2 ± 0.1 | 0.2 ± 0.1 | 0.3 ± 0.2 |
| Bone | 2.1 ± 1.8 | 0.5 ± 0.4 | 0.5 ± 0.2 | 0.6 ± 0.2 | 0.4 ± 0.2 |

TABLE 3

Biodistribution of Ga-67-IMP 241 given alone, with no bsAb pretargeting.

| Tissue | Time post-injection of Ga-67-IMP 241 peptide | | | | |
|---|---|---|---|---|---|
|  | 1 h | 2 h | 3 h | 4 h | 6 h |
| Tumor | 0.7 ± 0.4 | 0.3 ± 0.1 | 0.2 ± 0.1 | 0.2 ± 0.0 | 0.1 ± 0.0 |
| Liver | 0.1 ± 0.0 | 0.1 ± 0.0 | 0.1 ± 0.0 | 0.1 ± 0.0 | 0.1 ± 0.0 |
| Spleen | 0.0 ± 0.0 | 0.1 ± 0.1 | 0.1 ± 0.0 | 0.1 ± 0.0 | 0.1 ± 0.0 |
| Kidney | 2.2 ± 0.8 | 1.7 ± 0.5 | 2.6 ± 0.7 | 2.0 ± 0.4 | 2.6 ± 0.5 |
| Lungs | 0.1 ± 0.1 | 0.1 ± 0.1 | 0.1 ± 0.0 | 0.0 ± 0.0 | 0.1 ± 0.0 |

TABLE 3-continued

Biodistribution of Ga-67-IMP 241 given alone, with no bsAb pretargeting.

| Tissue | Time post-injection of Ga-67-IMP 241 peptide | | | | |
|---|---|---|---|---|---|
| | 1 h | 2 h | 3 h | 4 h | 6 h |
| Blood | 0.1 ± 0.0 | 0.1 ± 0.0 | 0.0 ± 0.0 | 0.0 ± 0.0 | 0.0 ± 0.0 |
| Stomach | 0.1 ± 0.1 | 0.0 ± 0.0 | 0.0 ± 0.0 | 0.1 ± 0.1 | 0.0 ± 0.0 |
| Sm. Intestine | 0.3 ± 0.3 | 0.1 ± 0.1 | 0.1 ± 0.1 | 0.3 ± 0.2 | 0.0 ± 0.0 |
| Lg. Intestine | 0.1 ± 0.0 | 0.0 ± 0.0 | 0.0 ± 0.0 | 0.5 ± 0.8 | 0.1 ± 0.0 |
| Bone | 0.1 ± 0.1 | 0.1 ± 0.0 | 0.1 ± 0.0 | 0.1 ± 0.0 | 0.0 ± 0.0 |

TABLE 4

Biodistribution of I-125-hMN-14 × 679-F(ab')$_2$ bispecific antibody with data reported in terms of T/NT ratios.

| Tumor-to-tissue ratio | Time post-injection of peptide (+24 h post-injection of bsAb) | | | | |
|---|---|---|---|---|---|
| | 1 h | 2 h | 3 h | 4 h | 6 h |
| Liver | 4.8 ± 2.3 | 5.5 ± 1.4 | 3.6 ± 1.9 | 6.4 ± 2.1 | 5.5 ± 3.3 |
| Spleen | 3.5 ± 2.1 | 4.6 ± 3.3 | 2.7 ± 0.9 | 4.6 ± 2.1 | 3.5 ± 2.2 |
| Kidney | 4.3 ± 1.6 | 5.0 ± 1.4 | 3.4 ± 1.5 | 5.8 ± 1.7 | 6.0 ± 3.7 |
| Lungs | 4.3 ± 1.7 | 5.8 ± 2.0 | 3.6 ± 1.8 | 5.7 ± 1.3 | 5.7 ± 3.3 |
| Blood | 2.1 ± 0.8 | 2.4 ± 0.7 | 2.2 ± 1.7 | 2.8 ± 0.6 | 2.5 ± 1.4 |
| Stomach | 1.2 ± 0.8 | 2.5 ± 1.2 | 1.5 ± 1.0 | 1.8 ± 0.5 | 1.9 ± 1.8 |
| Sm. Intestine | 9.0 ± 3.1 | 11.9 ± 2.3 | 7.7 ± 1.9 | 12.1 ± 2.3 | 12.4 ± 9.3 |
| Lg. Intestine | 9.5 ± 3.9 | 7.6 ± 1.9 | 5.2 ± 1.6 | 8.7 ± 0.9 | 8.6 ± 5.4 |
| Bone | 7.6 ± 4.7 | 10.1 ± 2.9 | 5.6 ± 2.9 | 10.2 ± 2.8 | 12.1 ± 9.3 |

TABLE 5

Biodistribution of Ga-67-IMP 241 given 24 hours after I-125-hMN-14 × 679-F(ab')$_2$ bispecific antibody.

| Tumor-to-tissue ratio | Time post-injection of peptide (+24 h post-injection of bsAb) | | | | |
|---|---|---|---|---|---|
| | 1 h | 2 h | 3 h | 4 h | 6 h |
| Liver | 8.0 ± 3.8 | 15.9 ± 8.9 | 13.1 ± 12.0 | 16.2 ± 8.6 | 16.0 ± 10.5 |
| Spleen | 10.7 ± 7.2 | 26.6 ± 28.7 | 16.3 ± 13.1 | 26.1 ± 23.4 | 17.4 ± 12.7 |
| Kidney | 2.3 ± 1.6 | 3.5 ± 2.2 | 2.4 ± 1.8 | 3.1 ± 1.1 | 4.3 ± 2.7 |
| Lungs | 4.5 ± 1.9 | 13.1 ± 7.5 | 11.4 ± 11.1 | 13.5 ± 5.9 | 20.2 ± 12.5 |
| Blood | 1.7 ± 0.8 | 6.1 ± 5.0 | 8.5 ± 9.5 | 8.7 ± 4.6 | 12.1 ± 8.0 |
| Stomach | 36.7 ± 22.8 | 52.8 ± 17.6 | 73.6 ± 47.4 | 56.9 ± 36.0 | 112.5 ± 60.7 |
| Sm. Intestine | 18.6 ± 9.1 | 27.7 ± 9.1 | 35.5 ± 26.0 | 22.0 ± 12.7 | 47.2 ± 35.9 |
| Lg. Intestine | 67.3 ± 44.1 | 74.2 ± 55.0 | 72.7 ± 89.0 | 56.5 ± 21.7 | 162.3 ± 270 |
| Bone | 11.5 ± 11.0 | 24.6 ± 15.1 | 17.8 ± 13.7 | 18.3 ± 3.1 | 53.0 ± 41.7 |

CITED REFERENCES

US Patents:

Kung, H. F. Gallium-labeled imaging agents. U.S. Pat. No. 5,079,346. Jan. 7, 1992.

Lee, T-W., Chen, W-L., Yu, M-D., Shen, L-H., Tsai, Z-T., Chyi, S-Y. Gallium mercaptosuccinate as a novel tumor imaging agent. U.S. Pat. No. 5,639,439 Jun. 17, 1997.

Other References of Interest:

Ambe, S. $^{68}$Ge-$^{68}$Ga generator with alpha-ferric oxide support. *Int. J. Appl. Radiat. Isot.*, 39:49–51, 1988.

Goodwin, D. A., Ransone, C. McK., Diamanti, C. I. and McTigue, M. Rapid synthesis and quality control of $^{68}$Ga-labeled chelates for clinical use. *Nucl. Med. Biol.*, 21:897–899, 1994.

Green, M. A., Mathias, C. J., Neumann, W. L., Fanwick, P. E., Janik, M. and Deutsch, E. A. Potential gallium-68 tracers for imaging the heart with PET: Evaluation of four gallium complexes with functionalized tripodal tris(salicylaldimine) ligands. *J. Nucl. Med.*, 34:228–233, 1993.

Greene, M. W. and Tucker, W. D. An improved gallium-68 cow. *J. Nucl. Med.*, 2:62–62, 1961.

Hanrahan, T., Yano, Y. and Welch, M. J. Long term study of high level Ge-68 generators. *J. Labelled Compd. Radiopharm.*, 19:1535, 1982.

Hnatowich, D. J. A method for the preparation and quality control of $^{68}$Ga radiopharmaceuticals. *J. Nucl. Med.*, 16:764–768, 1975).

Klivényi, G., Schuhmacher, J., Patzelt, E., Hauser, H. Matys, R., Moock, M., Regiert, T. and Maier-Borst, W. Gallium-68 chelate imaging of human colon carcinoma xenografts pretargeted with bispecific anti-CD44$_{V6}$/anti gallium chelate antibodies. *J. Nucl. Med.*, 39:1769–1776, 1998).

Kulprathipanja, S. and Hnatowich, D. J. A method for determining the pH stability range of gallium radiopharmaceuticals. *Int. J. Appl. Radiat. Isot.*, 28:229–233, 1977.

Kung, H. F., Liu, B. L., Mankoff, D., Kung, M. P., Billings, J. J., Francesconi, l. and Alavi, A. A new myocardial imaging agent: synthesis, characterization, and biodistribution of Ga-68-BAT-TECH. *J. Nucl. Med.*, 31:1635–1645, 1990.

Lee, J., Garmestani, K., Wu, C., Brechbiel, M. W., Chang, H. K., Choi, C. W., Gansow, O. A., Carrasquillo, J. A. and Paik, C. H. In Vitro and in vivo evaluation of structure-stability relationship of $^{111}$In and $^{67}$Ga-labeled antibody via 1B4M or C-NOTA chelates. *Nucl. Med. Biol.*, 24:225–230, 1997.

Lewis, R. E. and Camin, L. L. *J. Labelled Compd. Radiopharm.*, 18:164, 1981.

Loc'h, C. H., Maziere, B. and Comar, D. A new generator for ionic gallium68. *J. Nucl. Med.*, 21:171, 1980.

McElvaney, K. D., Hopkins, K. T. and Welch, M. J. Comparison of $^{68}$Ge/$^{68}$Ga generator systems for radiopharmaceutical production. *Int. J. Appl. Radiat. Isot.*, 35:521–524, 1984.

Neirinckx, R. D. and Davis, M. A. Potential column chromatography for ionic Ga-68. II: Organic ion exchangers as chromatographic supports. *J. Nucl. Med.*, 21:81–83, 1980.

Schuhmacher, J., Klivényi, G., Matys, R., Stadler, M., Regiert, T., Hauser, H., Doll, J., Maier-Borst, W. and Zöller, M. Multistep tumor targeting in nude mice using bispecific antibodies and a gallium chelate suitable for immunoscintigraphy with positron emission tomography. *Cancer Res.*, 55:115–123, 1995.

Sun, Y., Anderson, C. J., Pajeau, T., Reichert, D. E., Hancock, R. D., Motekaitis, R. J., Martell, A. E. and Welch, M. J. Indium(III) and gallium(III) complexes of bis(aminoethanethiol) ligands with different denticities: stabilities, molecular modeling and in vivo behavior. *J. Med. Chem.*, 39:458–470, 1996.

Wu, C., Jagoda, E., Brechbiel, M., Webber, K. O., Pastan, I., Gansow, O. and Eckelman, W. C. Biodistribution and catabolism of Ga-67-labeled anti-Tac dsFv fragment. *Bioconjugate Chem.*, 8:365–369, 1997.

Tsang, B. W., Mathias, C. J. and Green, M. A. A gallium-68 radiopharmaceutical that is retained in myocardium: $^{68}$Ga [(4,6-MeO$_2$sal)$_2$BAPEN]$^+$. *J. Nucl. Med.*, 34:1127–1131, 1993.

It will be apparent to those skilled in the art that various modifications and variations can be made to the products, compositions, methods, and processes of this invention. Thus, it is intended that the present invention cover such modifications and variations, provided they come within the scope of the appended claims and their equivalents. The disclosure of all publications cited above are expressly incorporated herein by reference in their entireties to the same extent as if each were incorporated by reference individually.

What is claimed is:

1. A targeting agent for positron emission tomography comprising a complex of gallium-68 with a single chelating agent linked via a peptidyl spacer to one or more HSG units, wherein said agent is a macrocyclic chelating agent.

2. The targeting agent of claim 1, wherein said Ga-68 associates with a 1,4,7-triazacyclononane-N,N',N''-triacetic acid (NOTA) or 1,4,7,10-tetraazacyclododecane-N,N', N''', N'''-tetraacetic acid (DOTA) moiety, linked via said peptidyl spacer to one or more HSG recognition units.

3. The targeting agent of claim 1, wherein the macrocyclic chelating agent complexed with gallium-68 and linked via a peptidyl spacer to one or more recognition units recognized by said multispecific targeting antibody has the formula:

4. The targeting agent of claim 1, wherein the macrocyclic chelating agent complexed with gallium-68 and linked via a peptidyl spacer to one or more recognition units recognized by said multispecific targeting antibody has the formula:

DOTA-Phe-Lys(HSG)-D-Tyr-Lys(HSG)-NH2.

5. A method of detecting a condition comprising: a) administering to a subject in need thereof a multispecific targeting agent having at least one binding site for a histaminyl-succinyl-glycyl moiety together with at least one binding site with affinity for an antigenic determinant on target tissue related to the condition to be detected, and b) sometime later, administering a Ga-68 radiolabeled targeting agent of claim 1, and c) imaging the subject using positron emission tomography; wherein said condition is cancer, thrombosis, stroke, atherosclerotic plaque, infection or inflammation.

6. The method of claim 5, further comprising treating the condition being detected.

7. The method as claimed in claim 5, wherein the multispecific targeting agent is hMN-14×679 F(ab')$_2$ 8. A method of preparing a Ga-68 labeled targeting agent by combining eluate from an acid-eluted Ge-68 Ga-68 generator and a NOTA- or DOTA-containing targetable agent.

9. The method of claim 8, further comprising preparing a Ga-68 labeling targeting agent by directly eluting an acid-eluted Ge-68/ Ga-68 generator into a vial containing a NOTA- or DOTA-targetable agent.

10. The method of claim 8, further comprising use of an anion-exchange step to remove unwanted tin, titanium or other metals from a generator eluate.

11. The method of claim 8, further comprising the use of a dilute acid for generator elution.

12. The method of claim 8, wherein a 0.5–1N hydrochloric acid solution is used for generator elution.

13. The method of claim 8, further comprising elution of the generator eluate into a pH neutral ammonium acetate solution containing enough ammonium acetate to substantially establish the pH of the final labeling solution at between three and six.

14. The method of claim 8, wherein the NOTA- or DOTA-containing targetable conjugate is selected from NOTA- and DOTA-conjugated peptides, polypeptides, proteins, carbohydrates, cytokines, hormones and cell receptor-binding agents.

15. The method of claim 8, wherein the NOTA-containing targetable conjugate is selected from peptides, polypeptides and proteins targeting somatostatin, LHRH, VIP, BLyS, and gastrin receptors.

16. The method of claim 8, wherein the NOTA-containing targetable conjugate is selected from peptides, polypeptides and proteins that target disease-associated antigens.

17. The method of claim 8, wherein the NOTA-containing targetable conjugate targets a tumor-associated antigen.

18. A composition comprising a NOTA- or DOTA-targeting agent conjugate dissolved in sufficient pH neutral ammonium acetate to enable substantially complete incorporation of Ga-68 when admixed with a solution of Ga-68 in dilute acid.

19. The composition of claim 18, wherein the NOTA- or DOTA-containing targetable conjugate is recognized by a primary targeting agent bearing at least one secondary recognition unit that recognizes an epitope of the NOTA- or DOTA-containing targetable conjugate.

20. The composition of claim 19, wherein the NOTA- or DOTA-containing targetable conjugate is recognized by a multispecific antibody bearing at least one secondary recognition arm that recognizes an epitope of the NOTA- or DOTA-containing targetable conjugate.

21. The composition of claim 20, wherein the multispecific antibody is comprised of a bispecific antibody or bispecific antibody fragment.

22. The composition of claim 21, wherein the NOTA or DOTA-containing targetable conjugate additionally contains at least one histaminyl-succinyl-glycyl-(HSG) recognition units attached to an epsilon lysine moiety and the bispecific antibody has at least one arm that recognizes the histaminyl-succinyl-glycyl- subunit when attached to an epsilon lysine moiety.

23. The composition of claim 22, wherein the NOTA-containing targetable conjugate is NOTA-2-benzylthioureayl-D-Ala-Lys(HSG)-Tyr-Lys(HSG)-amide.

24. The composition of claim 23, wherein any of the amino acids of the peptidyl backbone are in either the L- or D- configuration.

25. The composition of claim 22, wherein the DOTA-containing targetable conjugate is DOTA-Phe-Lys(HSG)-D-Tyr-Lys(HSG)-amide.

26. The composition of claim 25, wherein any of the amino acids of the peptidyl backbone are in either the L- or D- configuration.

27. The composition of claim 22, wherein the NOTA or DOTA-containing targetable conjugate has a concentration of about 1 micromolar or above in the composition.

28. The composition of claim 20, wherein the multispecific antibody is prepared by means of chemical cross-linking, quadroma technology, or as a construct of molecular biology.

29. The composition of claim 28, wherein the multispecific antibody is murine, chimeric, humanized or human in origin.

30. A kit comprising sufficient macrocycle-conjugated targeting agent to bind added acidic Ga-68 together with sufficient ammonium acetate buffer to substantially neutralize excess acid, and allow Ga-68 complexation by the macrocycle.

31. The kit of claim 30, further comprising a Ge-68/Ga-68 generator equipped for acid elution.

32. The kit of claim 30, wherein the gallium-68 generator eluate, once added, essentially forms a quantitative radiolabeling of the kit contents within about one hour.

33. The kit of claim 30, wherein the components are provided in liquid form, frozen, or lyophilized.

34. The kit of claim 30, wherein the components are heated to between 45 and 100 degrees Celsius for up to one hour to effect radiolabeling.

35. A method of detecting a condition comprising: a) administering to a subject in need thereof a multispecific targeting agent having at least one binding site for a histaminyl-succinyl-glycyl moiety together with at least one binding site with affinity for an antigenic determinant on target tissue related to the condition to be detected, and b) sometime later, administering a Ga-67 radiolabeled targeting agent of claim 1, and c) imaging the subject using single photon emission computed tomography; wherein said condition is cancer, thrombosis, stroke, atherosclerotic plaque, infection or inflammation.

36. A kit comprising sufficient macrocycle-conjugated targeting agent to bind added acidic Ga-67 together with sufficient ammonium acetate buffer to substantially neutralize excess acid, and allow Ga-67 complexation by the macrocycle.

* * * * *